United States Patent [19]

Laske et al.

[11] Patent Number: 5,728,149
[45] Date of Patent: Mar. 17, 1998

[54] INTEGRAL SPIRAL BAND ELECTRODE FOR TRANSVENOUS DEFIBRILLATION LEADS

[75] Inventors: Timothy G. Laske, Shoreview; Matthew D. Bonner, Plymouth; Jon M. Ocel, New Brighton, all of Minn.

[73] Assignee: Medtronic, Inc., Minneapolis, Minn.

[21] Appl. No.: 580,006

[22] Filed: Dec. 20, 1995

[51] Int. Cl.$^6$ .................................................. A61B 5/04
[52] U.S. Cl. .......................... 607/122; 607/116; 607/119; 128/642
[58] Field of Search ............... 607/119–124, 116, 607/118; 128/642

[56] References Cited

U.S. PATENT DOCUMENTS

| | | |
|---|---|---|
| 4,355,646 | 10/1982 | Kallok . |
| 4,481,953 | 11/1984 | Gold et al. .................. 607/123 |
| 4,603,705 | 8/1986 | Speicher et al. ............. 607/122 |
| 4,817,634 | 4/1989 | Holleman . |
| 4,860,769 | 8/1989 | Fogarty . |
| 4,865,037 | 9/1989 | Chin . |
| 4,932,407 | 6/1990 | Williams . |
| 4,951,687 | 8/1990 | Ufford . |
| 4,971,070 | 11/1990 | Holleman . |
| 5,042,143 | 8/1991 | Holleman . |
| 5,044,374 | 9/1991 | Lindemans . |
| 5,090,422 | 2/1992 | Dahl . |
| 5,191,901 | 3/1993 | Dahl . |
| 5,239,999 | 8/1993 | Imran . |
| 5,246,014 | 9/1993 | Williams . |
| 5,265,623 | 11/1993 | Kroll . |
| 5,271,417 | 12/1993 | Swanson . |
| 5,330,521 | 7/1994 | Cohen ........................... 607/122 |
| 5,370,644 | 12/1994 | Langberg ...................... 128/642 |
| 5,406,946 | 4/1995 | Imran ............................ 128/642 |
| 5,417,208 | 5/1995 | Winkler ........................ 607/122 |
| 5,423,884 | 6/1995 | Nyman et al. ................ 607/122 |
| 5,439,485 | 8/1995 | Mar . |

Primary Examiner—Jennifer Bahr
Assistant Examiner—David Ruddy
Attorney, Agent, or Firm—Reed A. Duthler; Harold R. Patton

[57] ABSTRACT

A cardioversion/defibrillation lead, and method of manufacture thereof, for location in a human heart. An elongated lead body having an insulating outer sheath extends between proximal and distal ends thereof, and an elongated defibrillation conductor within the lead body extends from a connector at the proximal end to a distal end at a predetermined location along the lead body length. A spiral band defibrillation electrode extends in spiral turns around the exterior of the insulating outer sheath for a pre-determined defibrillation electrode length. The defibrillation electrode is fabricated of a single tube of body compatible, electrically conductive material having first and second tube ends and an inside diameter selected to fit over the outer sheath and the internally disposed defibrillation lead conductor. At least one (and preferably a plurality) spiral slit is formed therein extending from first and second slit end points, spaced from the first and second ends, respectively, thereby forming at least one spiral band integrally attached to first and second end bands, respectively. At least one of the first and second end bands is attached to the defibrillation lead conductor at or near the distal end thereof. In other embodiments, intermediate connection bands are formed along the length of the spiral band, and electrical connections are made between such intermediate connection bands and the defibrillation lead conductor.

28 Claims, 6 Drawing Sheets

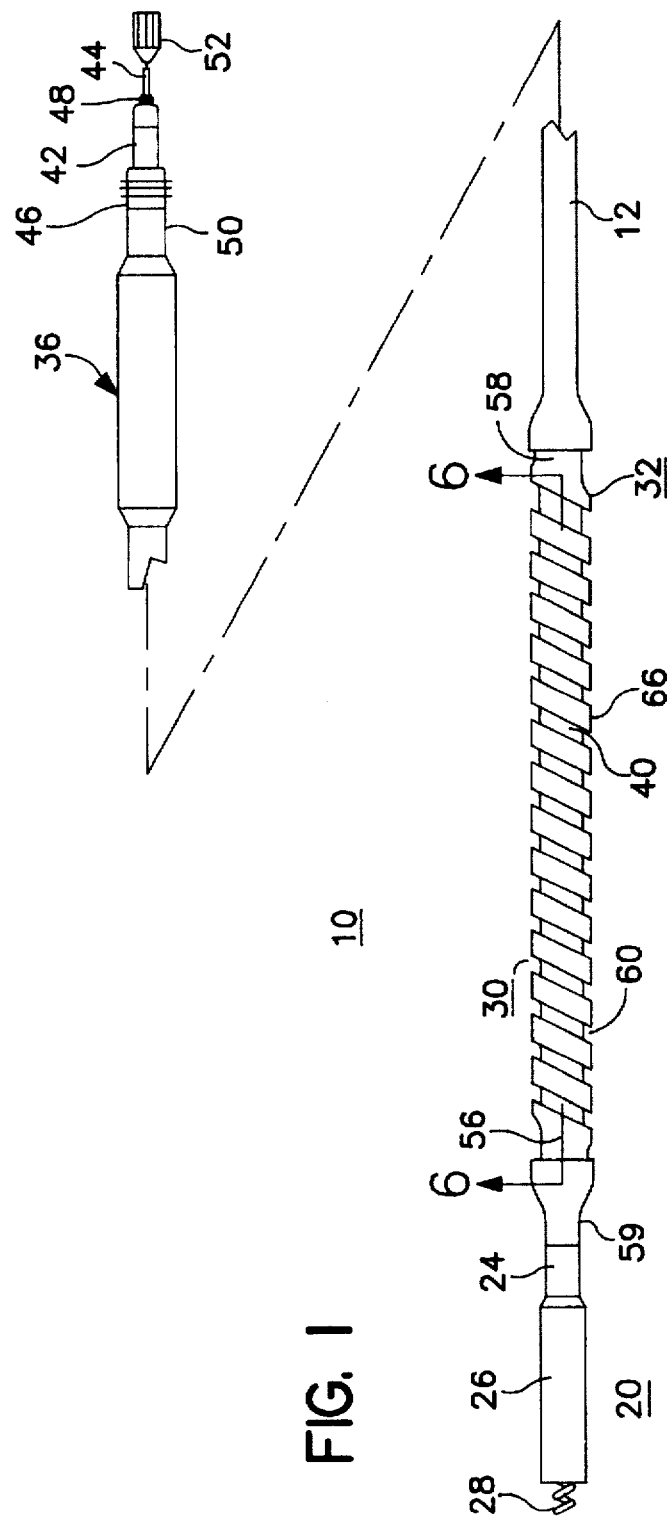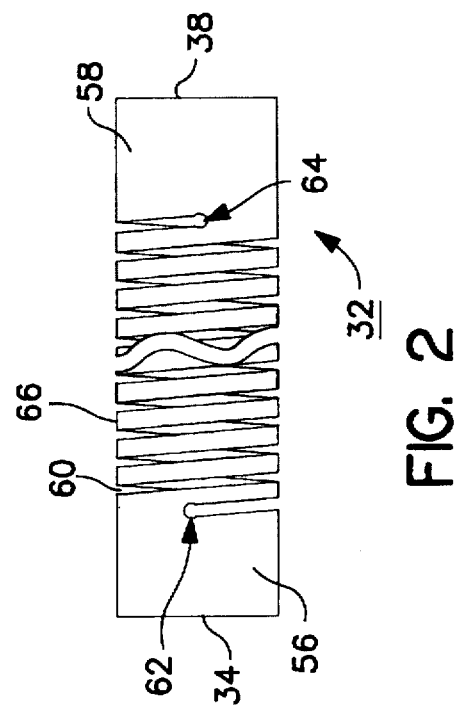
FIG. 1
FIG. 2

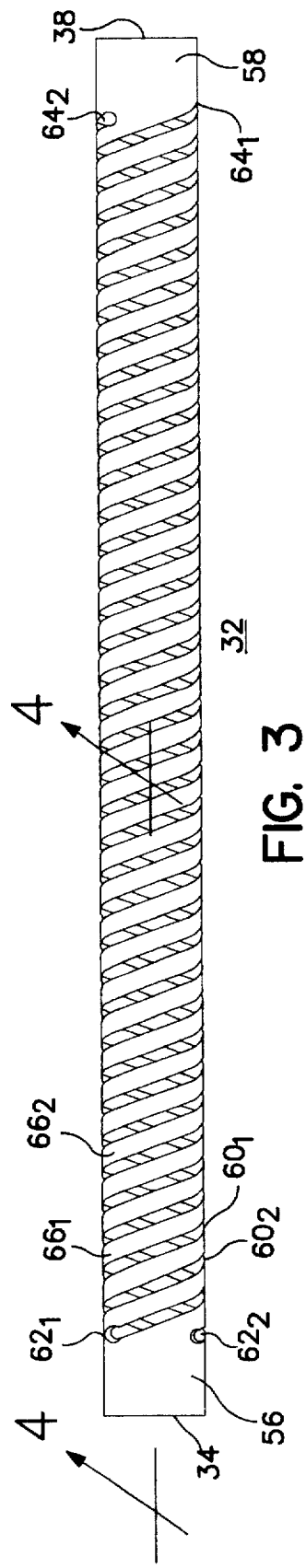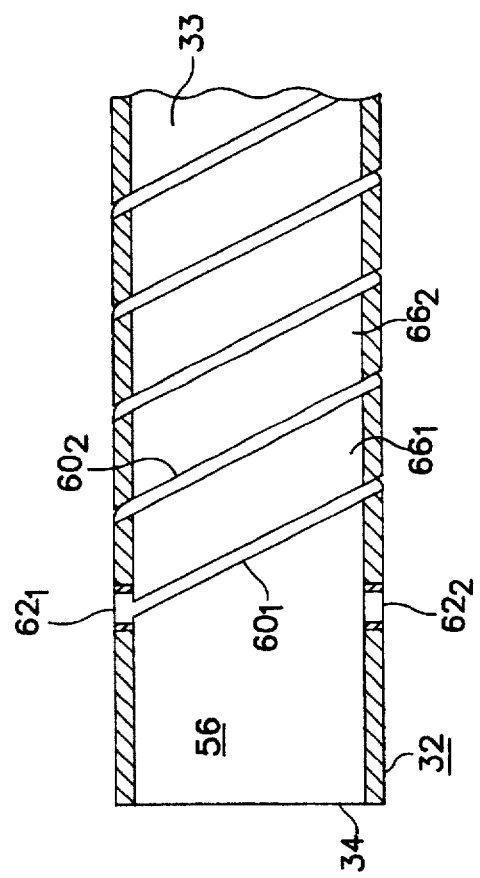
FIG. 3
FIG. 4

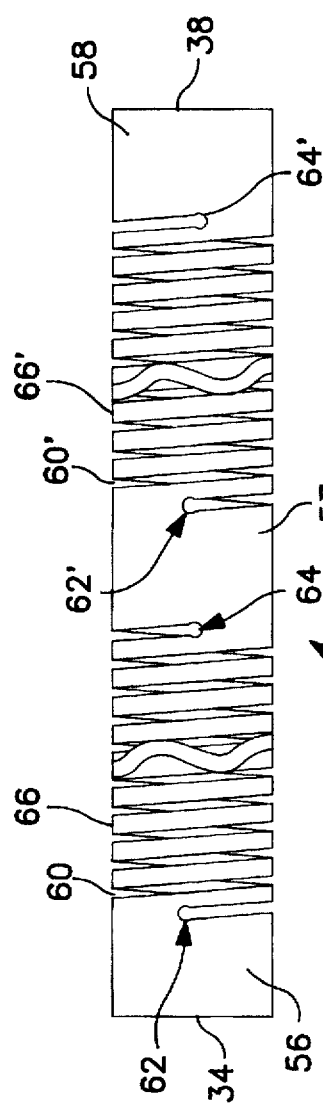
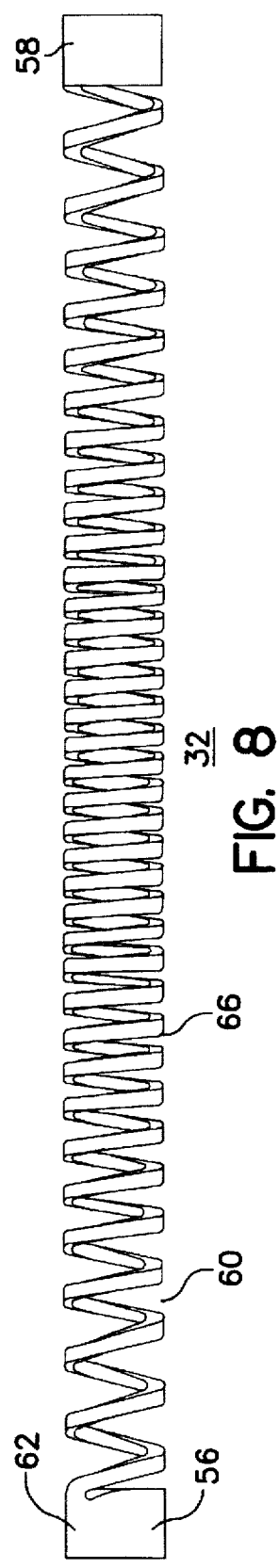
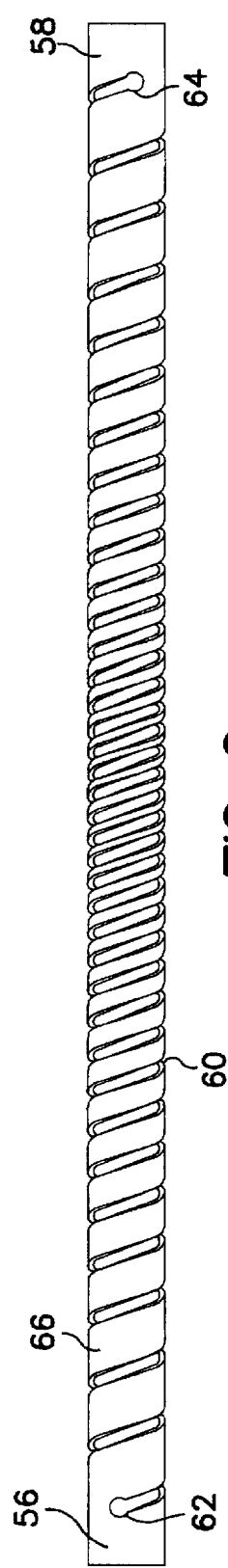
FIG. 7
FIG. 8
FIG. 9

INTEGRAL SPIRAL BAND ELECTRODE FOR TRANSVENOUS DEFIBRILLATION LEADS

FIELD OF THE INVENTION

The present invention relates to medical stimulators and leads generally, and more particularly to implantable defibrillation (including cardioversion) leads.

BACKGROUND OF THE INVENTION

Currently available implantable ventricular defibrillators, including the multi-programmable, pacemaker/cardioverter/defibrillator, typically employ epicardial or subcutaneous patch electrodes, alone, or in conjunction with one or more transvenously introduced endocardial leads with one or more electrodes disposed within a heart chamber or blood vessel. Ventricular defibrillation is typically effected with at least one electrode extending along an endocardial lead body disposed within the right ventricle and one or more additional defibrillation electrodes disposed outside the right ventricle to provide two or more defibrillation current pathways through the chamber of the heart to be defibrillated. Other endocardial defibrillation leads for transvenously introducing and positioning defibrillation electrodes into the right atrium and/or superior vena cava, the coronary sinus, the right outflow track or other locations in proximity to the heart have been disclosed in the prior art, including commonly assigned U.S. Pat. No. 4,932,407 to Williams.

Many versions of elongated defibrillation electrodes on a variety of endocardial lead body configurations have also been disclosed in prior patents and literature and employed clinically in patients. The requirements of an endocardial defibrillation electrode include a cross-section size and flexibility sufficient to facilitate transvenous introduction and withstand chronic flexing in situ, a metal alloy exhibiting high body compatibility for chronic implantation, low electrical resistance per unit cross-section area of the metal alloy, the capability of providing a relatively large exposed surface area to reduce impedance of the system and distribute the electrical current of the defibrillation shock in a desired pathway in relation to the vessel or chamber of implantation, ease of manufacture, and high reliability. The combination of the selection of materials, design of the electrode configuration and the supporting lead body, and the construction methods employed contribute to achieving these requirements.

After many years of development, the typical endocardial lead defibrillation electrode is configured as an elongated, body compatible wire of high conductivity that is spirally space wound or close wound about the lead body for a length appropriate for the intended use. The spacing of the coil turns retains flexibility of the lead body along the length of the electrode and distributes the electrode surface area along the length thereof. The wire cross-section is typically circular, as shown in U.S. Pat. No. 5,042,143 to Holleman et al., or rectangular, as shown in U.S. Pat. No. 4,481,953 to Gold et al., U.S. Pat. No. 5,090,422 to Dahl et al., and U.S. Pat. No. 5,265,653 to Kroll et al., although other wire configurations, e.g. the wrapped coils of U.S. Pat. No. 5,439,485 to Mar et al. have also been proposed. The coiled wire electrode may be formed of a single wire or in a multi-filar configuration of interlaced wires as shown in certain embodiments of the '485 patent. The coiled wire turns are typically partially embedded into the underlying lead body insulation to mechanically stabilize the exposed coil turns and direct the defibrillation current outward of the lead body.

In addition, various types of epicardial defibrillation leads having multiple coiled wire electrodes emanating from a common connection or connections with the defibrillation lead conductor have been disclosed as shown in certain embodiments of the above referenced '422 and '485 patents and in U.S. Pat. No. 4,860,769 to Fogarty et al., U.S. Pat. No. 4,865,037 to Chin et al., U.S. Pat. No. 4,817,634 to Holleman and U.S. Pat. No. 5,044,374 to Lindemans et al. In the '634 and '374 patents, a "patch" lead is depicted having four electrically parallel, branching coiled wire conductors are arrayed in a flat supporting patch. The winding pitch of the wire coils is increased in the outermost two branches as compared to the innermost two branches which would have the effect of increasing the electrode surface area along the periphery of the patch, where the current density is typically concentrated in such electrodes.

The exposed defibrillation electrode must be electrically and mechanically attached at one or more point to a defibrillation lead conductor that extends proximally to a connector at the proximal end of the lead body. Typically, the defibrillation lead conductor is a coiled wire conductor, although straight wires of stranded wire filaments are also being used. In either case, one end or both ends of the spiral wound defibrillation electrode wire are attached to the lead conductor extending to the proximal end. The attachment(s) require a number of separate paris, and the attachment sleeves, cores and crimps involved may result in a cumbersome and unduly enlarged connection.

As shown in the '143 and '485 patents, the coiled wire ends are attached to sleeves by welding, crimping or the like, and at least one of the sleeves is adhered to the internal coiled wire conductor. In the '953 patent, the ends of the defibrillation electrode wire coil are schematically shown to be directly connected inside the lead body to the ends of internally disposed straight defibrillation lead conductors, but in practice, additional parts are needed to make a reliable connection with practical lead conductors.

The '623 patent discloses the electrical connection of a stranded wire filament cable, defibrillation lead conductor at a central point along the length of an exposed wire ribbon defibrillation electrode. The central connection purportedly alters the electrical field and current distribution of a defibrillation shock applied to the defibrillation electrode with respect to the heart vessel or chamber. The wire ribbon is formed of a continuous rectangular cross-section band wound over a lead body outer insulation sheath in a spiral and between a pair of separate electrode end rings. The separate end rings appear to restrain lengthwise expansion of the wire ribbon electrode.

A further commercially available Endotak® endocardial defibrillation lead is constructed with a similar ribbon wire electrode with similar end caps that are welded to the ends of the wire ribbon. The electrical connection to the defibrillation lead conductor is effected at one or both end caps. The '623 patent is directed to improving the electrical current distribution of such an electrode design by decreasing the edge effect current concentrations that can occur at the ends, particularly at the end(s) where the electrical connection(s) to the defibrillation lead conductor is made. It is asserted that such concentrated current densities may damage blood vessels of heart tissue in their vicinity.

Despite the improvements that have been proposed, it continues to be desirable to simplify transvenous defibrillation lead body construction and to make the resulting lead more reliable for long term implantation through reduction of separate parts and steps in the attachment of the defibrillation electrode with the defibrillation lead conductor.

Moreover, improvements are desirable in the defibrillation current distribution to diminish current density concentrations and to otherwise optimize the current distribution between the two or more defibrillation electrodes and through the heart chamber to be defibrillated.

SUMMARY OF THE INVENTION

Therefore, a primary object of a first aspect of the invention is directed toward the provision of a defibrillation lead with a simplified defibrillation electrode construction that reduces separate parts employed in the attachment of the defibrillation electrode with the defibrillation lead conductor, thereby reducing attachment steps and junctions and increasing lead body integrity and reliability.

A further object of a further aspect of the invention is directed toward improving the current distribution of such a defibrillation electrode and reducing current density concentrations.

In compliance therewith, the defibrillation lead preferably comprises an elongated lead body having an insulating outer sheath extends between proximal and distal ends thereof, and an elongated defibrillation conductor within the lead body extends from a connector at the proximal end to a distal end at a pre-determined location along the lead body length. A spiral band defibrillation electrode extends in spiral band turns around the exterior of an insulating outer sheath for a predetermined defibrillation electrode length.

The defibrillation electrode is fabricated of a single tubular member of body compatible, electrically conductive material having first and second tube ends and an inside diameter selected to fit over the outer sheath and the internally disposed defibrillation lead conductor. At least one spiral slit is formed therein extending from first and second slit end points, spaced from the first and second ends, respectively, thereby forming at least one spiral band integrally attached to first and second ring-shaped or annular end bands, respectively. The first and second slit end points are formed with rounded openings that may exceed the slit width for strain relief.

Preferably, a plurality of spiral slits are formed in the tubular member each extending from first and second slit end points, spaced from the first and second tube ends, respectively, thereby forming a like plurality of the spiral bands integrally attached to the first and second end bands, respectively.

In accordance with a further aspect of the invention, the spacing apart and/or pitch of the slit(s) are varied along the length of the tubular member to provide an optimal current distribution pattern for the blood vessel or chamber of implantation or other location of implantation vis-à-vis the location and configuration of the return defibrillation electrode or electrodes.

In one embodiment, at least one of the first and second annular end bands is used as a connection band and electrically connected to the defibrillation lead conductor at or near the distal end thereof. In a further embodiment, the electrical connection may be alternatively or additionally made at one or more intermediate connection bands along the spiral band, e.g. a center-most spiral band, of width sufficient to be used in making the connection. The pitch and/or width of the spiral slit bounding such an intermediate connection band may be altered in order to accommodate the electrical connection with the defibrillation lead conductor.

In a still further embodiment, one or more intermediate, ring shaped or annular, connection band may be defined by forming two or more sets of one or more spiral slits extending in accordance with any of the above embodiments only in defined segments along the length of the tubular member, separated by the so-defined or more connection band(s).

The electrical connections may be made directly by welding, crimping or the like to adhere the annular end or intermediate connection band(s) or the intermediate spiral band to the underlying defibrillation lead conductor without any additional parts. In the case of defibrillation lead conductors formed of solid, silver-cored, stranded wire filament cables filling the inside diameter of the connection band, it is possible to crimp the connection band to the cable extending through it. In the case of a smaller diameter stranded wire filament cable than the tubular member lumen, it is preferred to crimp a welding band over the cable, insert it within the connection band and then weld or adhere the welding band with the connection band.

The defibrillation lead of the present invention is particularly optimized for transvenous introduction and implantation with the electrode extending in a heart chamber and/or major blood vessel adjacent to the heart chamber in conjunction with one or more epicardial patch or subcutaneous patch electrodes or a subcutaneous electrode formed as part of or all of the outer housing or "can" of an implantable defibrillator.

BRIEF DESCRIPTION OF THE DRAWINGS

These and other objects, advantages and features of the present invention will be more readily understood from the following detailed description of the preferred embodiments thereof, when considered in conjunction with the drawings, in which like reference numerals indicate identical structures throughout the several views, and wherein:

FIG. 1 is a plan view of one embodiment of a defibrillation lead having an tubular member slit into one or more spiral bands between integral end bands attached to a defibrillation lead conductor according to a first aspect of the present invention;

FIG. 2 is a side view of a first embodiment of the tubular member of FIG. 1 slit into a single band having a fixed pitch and spiral band width integrally attached to the end bands thereof;

FIG. 3 is a side view of a second embodiment of the tubular member of FIG. 1 slit into dual spiral bands having a fixed pitch and spiral band width integrally attached to the end bands thereof;

FIG. 4 is an enlarged cross-section view of the tubular member of FIG. 3;

FIG. 7 is a side view of a fourth embodiment of the tubular member of FIG. 1 formed with end-to-end spiral band segments providing an intermediate annular ring for electrical connection to a defibrillation lead conductor;

FIG. 8 is a side view of a fifth embodiment of the tubular member of FIG. 1 formed with a first varying pitch pattern of the spiral slit(s) and separation of constant width spiral band(s) of the tubular member;

FIG. 9 is a side view of a sixth embodiment of the tubular member of FIG. 1 formed with a second varying pitch pattern of the spiral slit(s) and separation of variable width spiral band(s) of the tubular member;

DETAILED DESCRIPTION OF THE PREFERRED EMBODIMENTS

Figure 5:
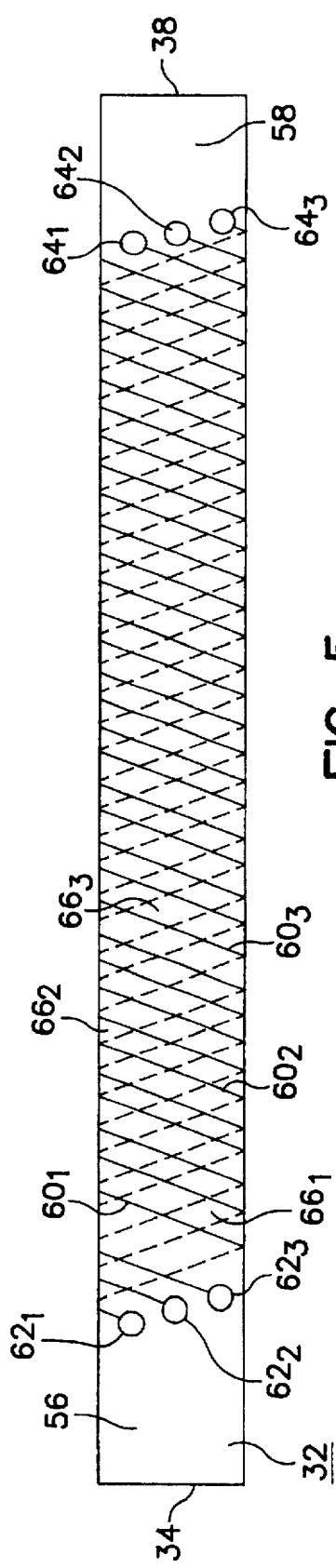
FIG. 5 is a side view of a third embodiment of the tubular member of FIG. 1 slit into three spiral bands having a fixed pitch and band width integrally attached to the end bands thereof.

FIG. 1 illustrates an overall view of a first preferred embodiment of the defibrillation lead 10 having a first embodiment of the defibrillation electrode 30 of the present invention formed thereon and illustrating a first preferred variable pitch for a particular current distribution. The straight distal end section of the defibrillation lead 10 is provided with a pace/sense electrode assembly 20 including an extendable helix, pace/sense electrode 28, mounted retractably within an insulating electrode head 26, and a ring shaped pace/sense electrode 24 forming a pace/sense electrode pair. A distal outer insulating sleeve 54 overlaps and stabilizes the distal end of the elongated, exposed defibrillation electrode 30 and terminates just proximal of the ring-shaped pace/sense electrode 24.

FIG. 1 also illustrates the proximal connector end of the defibrillation lead 10 having connector assembly 36 attached to a proximal outer insulating sheath 12. As depicted, electrical connector assembly 36 is a tri-polar in-line connector of the type conforming to the international connector standard designated "IS-1", but may be a bifurcated or trifurcated connector assembly of the type shown in the above-referenced '407 and '623 patents. The depicted electrical connector assembly 36 includes connector ring surfaces 42 and 50 and a hollow lumen, rotatable connector pin 44. Insulating segments 46 and 48 separate connector ring surfaces 42 and 50 and connector pin 44 and are each provided with a plurality of sealing rings for sealing the connector within the connector block of an associated implantable pacemaker/cardioverter/defibrillator.

Figure 6:
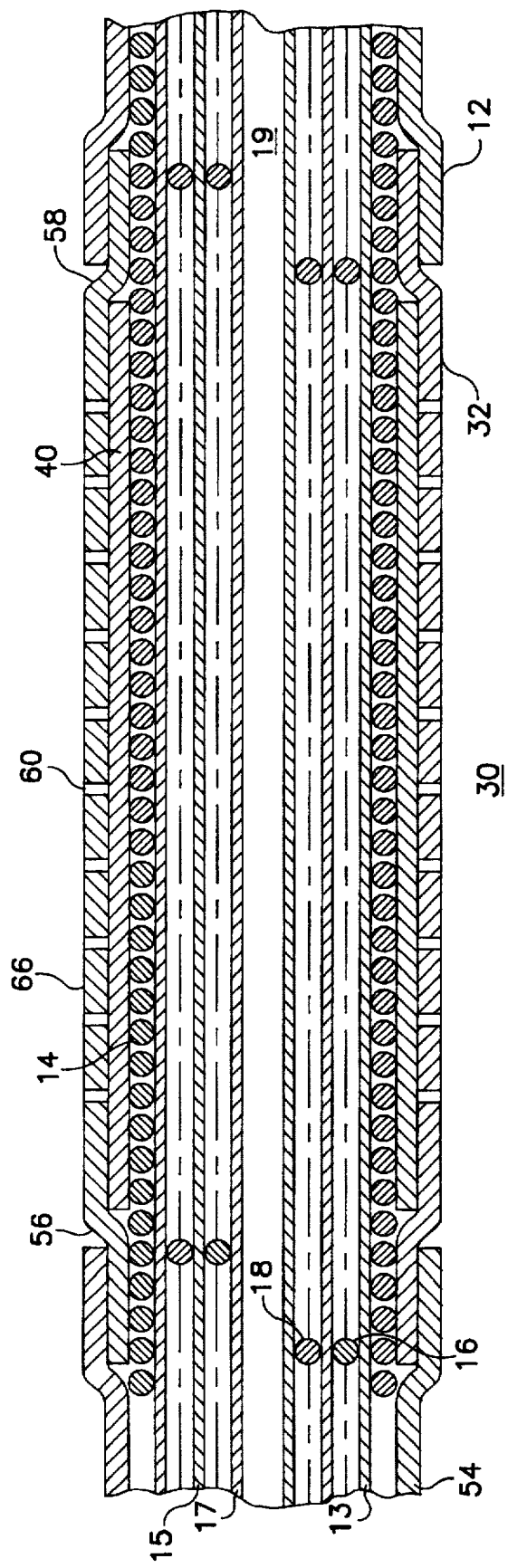
FIG. 6 is a side cross-section view of the lead of FIG. 1 with the tubular member of FIG. 2 taken along lines 6—6 of FIG. 1.

In this embodiment, proximal outer insulating sheath 12 encases three concentric, co-axial, coiled wire lead conductors 14, 16, 18, separated from one another by tubular insulating sheathes 13, 15, 17 and having a single interior lumen 19 as shown in FIG. 6. (In practice, the innermost sheath 17 around the inner lumen 19 is typically unnecessary.) This tri-polar, co-axial arrangement is illustrated in more detail in U.S. Pat. No. 4,355,646, issued to Kallok et al., incorporated herein by reference in its entirety. Alternatively, the pace/sense lead conductor coils 16 and 18 may be formed of electrically insulated wire coils wound together in a common diameter and an interlaced manner to reduce the overall diameter of the defibrillation lead body. As set forth in the '646 patent, the outer insulating sheath 12 and the interior insulating sheathes 13, 15, 17 employed in the depicted defibrillation lead 10 may be made of an implantable grade polyurethane or silicone rubber or other implantable, flexible plastic. The conductor coils 14, 16, 18 may be made of Drawn Brazed Strand wire (DBS), previously used in cardiac pacing leads or may be another low impedance conductor metal, such as a silver core MP35N alloy.

Returning to FIG. 1, the outermost defibrillation lead conductor coil 14 within proximal outer insulating sheath 12 is coupled to the somewhat enlarged distal connector ring surface 50. The middle pace/sense lead conductor coil 16 is coupled with the proximal connector ring surface 42. The innermost pace/sense lead conductor coil 18 is mechanically and electrically coupled to rotatable pin 44 such that rotation of pin 44 causes rotation of helical electrode 28 into or out of the distal end of electrode head 26. An appropriate structure for producing this IS-1 compatible, rotatable connector pin assembly illustrated may be found in U.S. Pat. No. 4,951,687 issued to Ufford et al., incorporated herein by reference in its entirety.

Connector pin 44 includes an axial lumen permitting passage of a wire stylet 52 down the innermost conductor coil 18 lumen located within insulating sheath 12, and to the distal end thereof. Passage of the stylet 52 through the lumen of the lead 10 assists in transvenously guiding it to its appropriate location in the heart chamber or vessel, and assists in maintaining the electrode head 26 in position while connector pin 44 is rotated to advance helical electrode 28 into the heart tissue. Insertion of the stylet 52 also straightens any pre-formed curvature in the defibrillation lead 10, including the defibrillation electrode 30, facilitating passage of the lead 10 through the venous system and heart structure. After the distal end of the lead 10 is anchored by means of electrode 28, the stylet 52 may be removed from the lumen of the lead, allowing the pre-formed curvature (if any) to be restored.

Turning to the construction of the defibrillation electrode 30, in accordance with a first aspect of the present invention, it is formed of an integral tubular member 32 of body compatible, electrically conductive material, e.g. platinum or a platinum alloy or a platinum coated titanium or tantalum conductor. The integral tubular member may take any of the configurations shown in the remaining figures and combinations and variations thereof and is electrically coupled to the defibrillation lead conductor, which may take forms other than the coiled wire conductor described above, through integral connection band or bands. As described below, the particular lead body and lead conductor configuration may vary considerably from the above described FIG. 1 embodiment of defibrillation lead 10.

The tubular member 32 has a first or distal tube end 34 and a second or proximal tube end 38 and a lumen 33 having an inside diameter selected to fit over the lead body and particularly, a separate, intermediate outer sheath 40 of the lead body insulating the internally disposed defibrillation lead conductor 14. As shown in FIG. 2, a spiral slit 60 is formed therein extending from first and second slit end points 62 and 64, spaced from the first and second ends 34 and 38, respectively, thereby forming at least one spiral band 66 integrally attached to first and second annular end bands 56 and 58, respectively. Preferably, both of the first and second end bands 56 and 58 can be used as connection bands and electrically connected to the defibrillation lead conductor 14 as shown in FIG. 6, for example.

Preferably, in one variation, a plurality of spiral slits $60_n$ are formed in the tubular member 32 each extending from first and second slit end points $62_n$ and $64_n$, spaced from the first and second tube ends 34 and 38, respectively, thereby forming a like plurality of the spiral bands $66_n$ integrally attached to the first and second annular end bands 56 and 58, respectively. FIG. 3 is a side view of a second embodiment of the tubular member of FIG. 1 slit into dual spiral bands $66_1$ and $66_2$ having a fixed pitch and band width integrally attached to annular end bands 56 and 58. FIG. 4 is an enlarged cross-section view of a portion of the tubular member of FIG. 3 along lines 4—4 thereof showing the spiral bands and the lumen 33 of the tubular member 32. FIG. 5 is a side view of a third embodiment of the tubular member of FIG. 1 slit into three spiral bands $66_1$, $66_2$ and $66_3$ having a fixed pitch and band width and integrally attached to the annular end bands 56 and 58. Any number of such bands may be employed as appropriate to a particular application.

The slit or slits $60_n$ are of a predetermined slit width, and the first and second slit end points $62_n$ and $64_n$ are formed with rounded and slightly enlarged openings exceeding the slit width for strain relief as also shown schematically in the embodiments of FIGS. 3–5.

It should also be noted more than one defibrillation electrode 30 may be formed along the lead body for connection with a common defibrillation lead conductor or separate defibrillation lead conductors. In this regard, a single elongated tubular member 32 may be formed to have at least two discrete spiral band electrode segments formed along it and separated by at least one annular intermediate band similar in function to annular end bands 56, 58. In one such embodiment, a single intermediate annular band may be provided and electrically connected to the defibrillation lead conductor with or without electrical connections at one or both of the annular end bands 56 and 58.

FIG. 7 is a side view of a fourth embodiment of the tubular member of FIG. 1 formed with end-to-end spiral band segments 66, 66' providing such an intermediate annular connection ring 57 for electrical connection to a defibrillation lead conductor. The end rings 56 and 58 may also be connected to the defibrillation lead conductor or may be insulated from it. Of course, a number of such spiral band segments 66, 66', etc., and intermediate annular bands may be formed integrally from the tubular member 32.

In accordance with a further aspect of the invention, the slit width and pitch of the slits $60_n$ of any of the above-described embodiments and variations thereof may be varied along the length of the tubular member 32 in order to provide variable spacings and widths of the spiral band(s) $66_n$ along the length thereof. The variation in band spacing and width results in a varying exposed surface area and affects charge density and current dispersion of the cardioversion shock electrical energy into the adjacent blood and cardiac tissue. For example, pitch and width variations of a single band 66 and slit 60 are illustrated in FIGS. 8 and 9.

FIG. 8 is a side view of a fifth embodiment of the tubular member 32 of FIG. 1 formed with a first varying pitch pattern of the spiral slit 60 and separation of constant width spiral band 66 formed from the tubular member 32. The pitch of the turns of the spiral band 66 and the slit 60 spacing increases from the center toward the end bands 56 and 58. The electrical connection is between one or both of the end bands 56, 58 with a defibrillation lead conductor.

FIG. 9 is a side view of a sixth embodiment of the tubular member 32 of FIG. 1 formed with a second varying pitch pattern of the spiral slit 60 and separation of variable width turns of the single spiral band 66 formed from the tubular member 32. The spiral slit 60 is of a constant width and increasing pitch approaching the center of the length of the tubular member 32. Therefore, the turns of the spiral band 66 widen progressively as the end bands 56 and 58 are approached. The electrical connection is again between one or both of the end bands 56, 58 with a defibrillation lead conductor.

It will be understood that any combination of the above patterns may be made with intermediate or central connection bands formed therein. It will also be understood that the intermediate annular bands, e.g. annular band 57 of FIG. 7, may be formed as a wide turn of spiral band 66 by varying the pitch and spacing of the slit 60.

Finally, asymmetric patterns of varying spiral band pitch and/or width and/or fixed or varying slit widths separating adjacent bands with respect to the end or intermediate connection bands are also contemplated by the present invention. For example, the spiral band pitch or width may increase from distal to proximal end band or from proximal to distal end band or from both end bands toward or away from one or more intermediate band. Other patterns will be apparent to those skilled in the art.

Each of the above described patterns of slit(s) and band(s) may be created in a solid tubular member 32 by mounting the tubular member for relative rotation with respect to a mechanical die in a lathe. Preferably, an electrical discharge machining (EDM) electrode is employed to electrically erode the material of the tubular member 32 into the slit(s) 60 and separate it into the spiral band(s) as the tubular member is rotated and advanced linearly with respect to the electrode in the manner of a lathe. In either case, computer controlled machining may be effected by relative rotation and axial displacement of the cutting tool or electrode with respect to the tubular member to form the spiral slit pitch and width pattern in accordance with stored pattern defining software in a manner well known in the art. Alternatively, the spiral slits may be etched from the single tubular member through a chemical milling process. A spiral band pattern may be masked on the exterior of the single tubular member while the interior lumen surface is entirely masked. Then, the tubular member may be exposed to an etching chemical to etch away the unmasked slits, and the resulting slit edges may be deburred to smooth them.

Returning to the manner in which the electrical and mechanical connection between the tubular member 30 and the defibrillation lead conductor 14 is effected, FIG. 6 depicts one preferred method of attachment consistent with the embodiment of FIG. 1. The lead body is assembled enclosing the lead conductor coils 14, 16 and 18 extending within the intermediate outer sheath 40. The tubular member 32 is fitted over the intermediate outer sheath 40, and the ends of the proximal outer sheath 12 and the distal outer insulating sheath 54 are temporarily retracted from the annular end bands 56 and 58. Electrical and mechanical attachment is effected by swaging down the end sections of annular end connection bands 56 and 58 against the underlying coil wire turns of the defibrillation lead conductor 18. Welding may also be used between the annular end bands 56 and 58 against the underlying coil wire turns of the defibrillation lead conductor 18.

In this example, the swaging necks down the diameter of the both end band sections to the outer diameters of the proximal outer sheath 12 and the distal outer sheath 54. The ends of proximal outer sheath 12 and the distal outer sheath 54 are then expanded and drawn over the necked down end band sections of end connector bands 56 and 58. Heat may be applied to seal the spiral bands 66, $66_n$ with the underlying intermediate insulating sheath 40 and the ends of proximal outer sheath 12 and the distal outer sheath 54 to the necked down end band sections. The resulting defibrillation electrode configuration enlarges the overall lead 10 diameter by twice the thickness of the tubular member 30 or less, resulting in a relatively isodiametric assembly.

Any of the other known methods of attachment may be employed to make the connection with the defibrillation lead conductor 14 without swaging down the sections of the end connection bands 56 and 58. The electrical connections may be made directly by welding to adhere the annular end or intermediate band(s) or the intermediate spiral band to the underlying defibrillation lead conductor 14. However no additional parts are needed by virtue of the integral fabrication of the spiral band 66, $66_n$ with the annular end bands 56 and 58.

Figure 10:
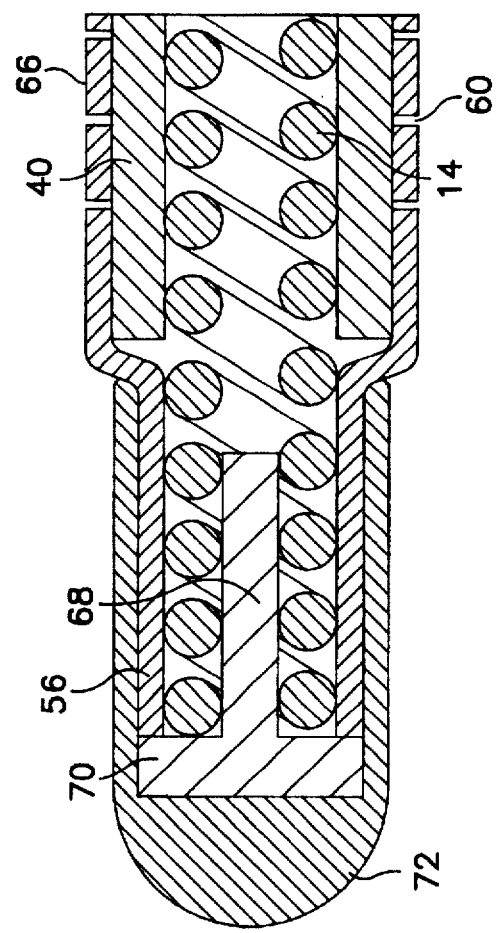
FIG. 10 is a side cross-section view of a further mechanism for making a distal end electrical and mechanical connection of a defibrillation lead conductor coil with a defibrillation electrode of the types depicted in any of the preceding FIGS. 1–9.

FIG. 10 is a side cross-section view of a further mechanism for making a distal end electrical and mechanical connection of a defibrillation lead conductor coil with a defibrillation electrode 30 of the type depicted in any of the above figures. In this embodiment, the defibrillation lead 10' does not include any distal pace/sense electrodes or respective pace/sense lead conductors. The annular end band 56 is extended within the distal outer sheath 54 to extend over the proximal extension 68 of a tip crimp core 70 and crimped to it. The proximal annular end band (not shown) may be attached to the defibrillation lead conductor 14 in the manner described above. The insulating end cap 72 is formed over the crimp core 70. Such a connection of the distal end of the defibrillation lead 10' with the distal end of the defibrillation electrode 30 may be useful in the CS or RV outflow track defibrillation leads and other endocardial defibrillation leads known in the art and described above and may also be employed in the fabrication of epicardial defibrillation leads as described above.

Alternatively, in the case of defibrillation lead conductors formed of solid core, silver-cored stranded wire filament cables filling the inside diameter of an end or intermediate connection band, it is possible to crimp the connection band to the cable extending through it. In other cases, it is preferred to crimp a welding band over the cable, insert it within the connection band and then weld or adhere the welding band with the connection band. Such silver-cored stranded wire filament cables are disclosed, for example, in commonly assigned U.S. Pat. No. 5,246,014 issued to Williams et al. and incorporated herein by reference in its entirety. The fine wire strands forming the multi-strand cable are preferably formed of a low resistance, high current capacity metal, e.g. platinum-iridium alloy or a composite, e.g. a silver core MP35N wire that may optionally be coated with platinum or the like.

In the case of a stranded wire filament cable, defibrillation lead conductor of the type described above, it would be possible to form the distal end of the elongated tubular member 32 with a closed end and a lumen just large enough to receive the end of the cable. The cable could be inserted into the lumen of the closed end and the assembly crimped together. In such a case, the distal closed end of the elongated tubular member could be insulated or left uninsulated.

Figure 11:
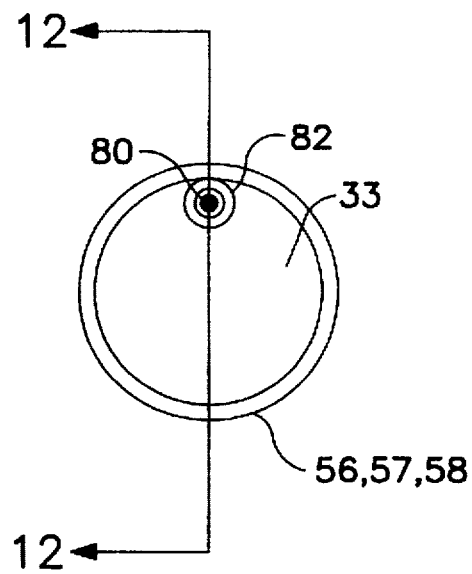
FIG. 11 is an end view of a further attachment mechanism for making an electrical and mechanical connection of a stranded wire filament cable defibrillation lead conductor with an end or intermediate connection band.
Figure 12:
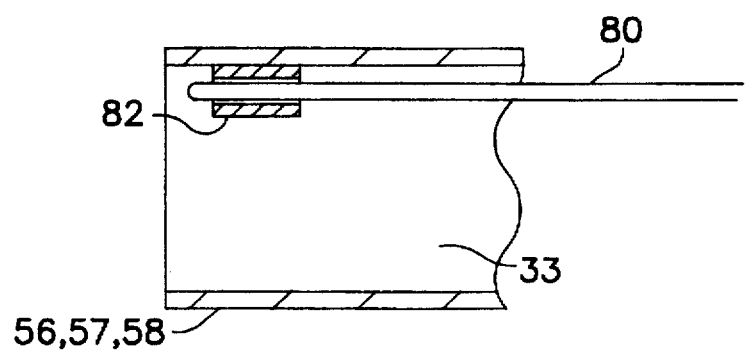
FIG. 12 is a side cross section view depicting the attachment mechanism and cable of FIG. 11.

FIGS. 11 and 12 depict a further mechanism and method of connecting a small diameter, multi-strand, wire filament cable 80 of the type described above to any of the end or intermediate annular connection bands 56, 57, 58 for any of the above-described defibrillation electrode configurations. A tubular attachment member 82 is formed within the annular connection band lumen which is coextensive with the lumen 33 of the single tubular member 32 that the band is formed integrally with. The end of the wire filament cable 80 extends through the tubular attachment member and is electrically and mechanically attached thereto by crimping or welding.

The attachment member may alternatively be formed of a tab or the like formed of a section of the end or intermediate connection band that extends into the lumen 33 to wrap around the stranded wire filament cable 80. The tab may be formed by machining or etching in the manner that the spiral band is formed to have a length that is then deformed in an arc inside the lumen 33 to encircle the cable 80 between it and the connection band.

Although the lead body and defibrillation electrode 30 are shown in a straight configuration in the figures, it will be understood that they may be formed in any shape, including a U-shape, a J-shape, a spiral shape, etc., selected in order to optimally position the defibrillation electrode in a heart chamber or vessel.

Although the defibrillation electrode 30 of the present invention has particular application in an endocardial defibrillation lead, it will be understood that it may be employed in epicardial, subcutaneous, and submusculature electrode configurations of any of the known types, including those disclosed in the above-referenced patents.

While there has been shown what are considered to be the preferred embodiments of the invention, it will be manifest that many changes and modifications may be made therein without departing from the essential spirit of the invention. The disclosed lead and electrode configurations, manufacturing methods and attachment means and methods should be considered exemplary, rather than limiting with regard to the interpretation of the following claims. It is intended, therefore, in the following claims to cover all such changes and modifications as may fall within the true scope of the invention.

PARTS LIST FOR FIGS. 1–12 defibrillation lead 10
proximal outer insulating sheath 12
outer coiled wire defibrillation lead conductor 14
insulating sheathes 13, 15, 17
middle coiled wire pace/sense lead conductor 16
inner coiled wire pace/sense lead conductor 18
inner lumen 19
pace/sense electrode assembly 20
ring shaped pace/sense electrode 24
insulating electrode head 26
extendable helix, pace/sense electrode 28
defibrillation electrode 30
single tubular member 32
tubular member lumen 33
distal tube end 34
electrical connector assembly 36
proximal tube end 38
intermediate outer sheath 40
includes connector ring surface 42
rotatable connector pin 44
insulating segments 46, 48
connector ring surface 50
wire stylet 52
distal outer insulating sheath 54
end bands 56, 58
intermediate band 57
slit 60, $60_n$
first slit end point 62, $62_n$
second slit end points 64, $64_n$
spiral bands 66, $66_n$
proximal extension 68
tip crimp core 70
insulating end cap 72
standed wire filament cable 80
attachment member 82

We claim:

1. A defibrillation lead for location in a human heart of the type comprising:
   an elongated lead body extending between a connector at a proximal end thereof and to a distal end thereof;
   an elongated defibrillation conductor within said lead body extending from said connector to a conductor distal end at a pre-determined location along the length of said lead body;
   a defibrillation electrode extending in spiral turns of at least one spiral band around the exterior of said lead body for a pre-determined defibrillation electrode length, said defibrillation electrode fabricated of a single tubular member of body compatible, electrically conductive material having first and second ends and first and second tubular end bands adjacent said first and second ends and a lumen with an inside diameter selected to fit over said lead body, said single tubular member further including at least one spiral slit formed therein extending from first and second slit end points, spaced from said first and second ends, respectively, thereby forming said at least one spiral band integrally attached to first and second end bands, respectively; and
   means for attaching at least one of said first and second end bands of said defibrillation electrode to said defibrillation lead conductor.

2. A defibrillation lead according to claim 1 wherein said tubular member includes a plurality of spiral slits formed therein each extending from first and second slit end points, spaced from said first and second ends, respectively, thereby forming a like plurality of said spiral bands integrally attached to said first and second end bands, respectively.

3. A defibrillation lead according to claim 2 wherein said slits are of a predetermined slit width and said first and second slit end points are formed with enlarged openings exceeding said slit width.

4. A defibrillation lead according to claim 2 wherein:
   said defibrillation lead conductor comprises a coiled wire conductor extending within the lumen of at least one of said end bands of said single tubular member; and
   said attaching means comprises welds of at least one of said first and second end bands over and against said coiled wire conductor within said lumen.

5. A defibrillation lead according to claim 2 wherein said defibrillation lead conductor comprises a stranded wire cable conductor extending at least within one of said end bands of said single tubular member.

6. A defibrillation lead according to claim 5 wherein said attaching means comprises:
   means formed integrally with said one of said end bands and extending within said lumen of said single tubular member and around said stranded wire cable conductor.

7. A defibrillation lead according to claim 2 wherein;
   said defibrillation lead conductor comprises a stranded wire filament cable conductor having an outer diameter substantially filling said lumen of at least one of said end bands of said single tubular member; and
   said attaching means comprises a crimp of said at least one end band against said stranded wire filament cable conductor.

8. A defibrillation lead according to claim 2 wherein said slits are spaced by separations varying along the length of said single tubular member thereby varying the widths of said spiral bands between said first and second end bands.

9. A defibrillation lead according to claim 2 wherein the spacing apart and pitch of said slits are varied along the length of said single tubular member.

10. A defibrillation lead according to claim 2 wherein the widths of said slits are varied along the length of the tubular member.

11. A defibrillation lead according to claim 1 wherein said slits adjacent to said end bands are of a predetermined slit width and said first and second slit end points are formed with enlarged openings exceeding said slit width.

12. A defibrillation lead according to claim 1 wherein:
    said defibrillation lead conductor comprises a coiled wire conductor extending within the lumen of at least one of said end bands of said single tubular member; and
    said attaching means comprises welds of at least one of said first and second end bands over and against said coiled wire conductor within said lumen.

13. A defibrillation lead according to claim 1 wherein said defibrillation lead conductor comprises a stranded wire cable conductor extending at least within one of said end bands of said single tubular member.

14. A defibrillation lead according to claim 13 wherein said attaching means comprises:
    means formed integrally with said one of said end bands and extending within said lumen of said single tubular member and around said stranded wire cable conductor.

15. A defibrillation lead according to claim 1 wherein;
    said defibrillation lead conductor comprises a stranded wire filament cable conductor having an outer diameter substantially filling said lumen of at least one of said end bands of said single tubular member; and
    said attaching means comprises a crimp of said at least one of said end bands against said stranded wire filament cable conductor.

16. A defibrillation lead according to claim 1 wherein said slit is spaced by a separation varying along the length of said single tubular member thereby varying the width of said spiral band between said first and second end bands.

17. A defibrillation lead according to claim 1 wherein the spacing apart and pitch of said slit are varied along the length of said single tubular member.

18. A defibrillation lead according to claim 1 wherein the slit width is varied along the length of the tubular member.

19. A defibrillation lead for location in a human heart of the type comprising:
    an elongated lead body extending between a connector at a proximal end thereof and to a distal end thereof;
    an elongated defibrillation conductor within said lead body extending from said connector to a conductor distal end at a pre-determined location along the length of said lead body;
    a defibrillation electrode extending in spiral turns of at least one spiral band around the exterior of said lead body for a pre-determined defibrillation electrode length, said defibrillation electrode fabricated of a single tubular member of body compatible, electrically conductive material having first and second ends and first and second tubular end bands adjacent said first and second ends and a lumen with an inside diameter selected to fit over said lead body, said single tubular member further including at least one spiral slit formed therein extending from first and second slit end points, spaced from said first and second ends, respectively, thereby forming said at least one spiral band integrally attached to first and second end bands, respectively; and
    means for attaching at least one of said first and second end bands of said defibrillation electrode to said defibrillation lead conductor, said slit formed by machining away material of said single tubular member.

20. A defibrillation lead for location in a human heart of the type comprising:

an elongated lead body extending between a connector at a proximal end thereof and to a distal end thereof;

an elongated defibrillation conductor within said lead body extending from said connector to a conductor distal end at a pre-determined location along the length of said lead body;

a defibrillation electrode extending in spiral turns of at least one spiral band around the exterior of said lead body for a pre-determined defibrillation electrode length, said defibrillation electrode fabricated of a single tubular member of body compatible, electrically conductive material having first and second ends and first and second tubular end bands adjacent said first and second ends and a lumen with an inside diameter selected to fit over said lead body, said single tubular member further including at least one spiral slit formed therein extending from first and second slit end points, spaced from said first and second ends, respectively, thereby forming said at least one spiral band integrally attached to first and second end bands, respectively; and means for attaching at least one of said first and second end bands of said defibrillation electrode to said defibrillation lead conductor, said slit formed by chemically etching away material of said single tubular member.

21. A defibrillation lead for location in a human heart of the type comprising:

an elongated lead body extending between a connector at a proximal end thereof and to a distal end thereof;

an elongated defibrillation conductor within said lead body extending from said connector to a conductor distal end at a pre-determined location along the length thereof;

a defibrillation electrode extending in spiral turns of at least one spiral band around the exterior of said lead body for a pre-determined defibrillation electrode length, said defibrillation electrode fabricated of a single tubular member of body compatible, electrically conductive material having first and second ends and first and second tubular end bands adjacent said first and second ends and a lumen with an inside diameter selected to fit over said lead body, said single tubular member further including at least one spiral slit formed therein extending from first and second slit end points, spaced from said first and second ends, respectively, thereby forming said at least one spiral band integrally attached to first and second end bands, respectively; and at least one intermediate connection band formed of a spiral band turn between said first and second end bands; and means for attaching said at least one intermediate connection band of said defibrillation electrode to said defibrillation lead conductor.

22. A defibrillation lead according to claim 21 wherein the slit width is varied along the length of the tubular member.

23. A defibrillation lead according to claim 21 wherein said slit is spaced by a separation varying along the length of said single tubular member thereby varying the width of said spiral band between said first and second end bands.

24. A defibrillation lead according to claim 21 wherein the spacing apart and pitch of said slit are varied along the length of said single tubular member.

25. A defibrillation lead for location in a human heart of the type comprising:

an elongated lead body extending between a connector at a proximal end thereof and a distal end thereof;

an elongated defibrillation conductor within said lead body extending from said connector to a conductor distal end at a pre-determined location along the length thereof;

a defibrillation electrode extending for a pre-determined defibrillation electrode length, said defibrillation electrode fabricated of a single tubular member of body compatible, electrically conductive material having first and second ends and first and second segments between the first and second ends and first and second tubular end bands adjacent said first and second ends and a lumen of an inside diameter selected to fit over said lead body, said tubular member further including at least first and second spiral slits formed therein in the first and second segments, respectively, extending from first and second slit end points spaced from said first and second ends, respectively, to third and fourth end points spaced from one another between said first and second segments along the length of said tubular member, thereby forming said at least two, end-to-end spiral bands integrally attached to first and second end bands, respectively, and joined at an intermediate band bounded by said third and fourth end points; and means for attaching at least one of said first and second end bands and said intermediate band of said defibrillation electrode to said defibrillation lead conductor.

26. A defibrillation lead according to claim 25 wherein at least one of said first and second spiral bands in said first and second segments is formed of a plurality of spiral bands separated by a plurality of spiral slits formed in the respective segment of said tubular member.

27. A defibrillation lead according to claim 25 wherein said first and second slits are spaced by a separation varying along the lengths of said first and second segments of single tubular member thereby varying the widths of said first and second spiral bands along said first and second segments.

28. A defibrillation lead according to claim 25 wherein the spacings apart and pitches of said first and second slits are varied along the lengths of said first and second segments of said single tubular member.

* * * * *